United States Patent
Lee et al.

(10) Patent No.: US 11,008,599 B2
(45) Date of Patent: May 18, 2021

(54) VARIANT PHOSPHORIBOSYLPYROPHOSPHATE AMIDOTRANSFERASE AND METHOD OF PREPARING PURINE NUCLEOTIDE USING THE SAME

(71) Applicant: CJ CHEILJEDANG CORPORATION, Seoul (KR)

(72) Inventors: Ji Hye Lee, Anyang-si (KR); So-jung Park, Suwon-si (KR); Min Ji Baek, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/493,661

(22) PCT Filed: Jul. 19, 2019

(86) PCT No.: PCT/KR2019/008924
§ 371 (c)(1),
(2) Date: Sep. 1, 2020

(87) PCT Pub. No.: WO2020/196993
PCT Pub. Date: Oct. 1, 2020

(65) Prior Publication Data
US 2021/0047666 A1    Feb. 18, 2021

(30) Foreign Application Priority Data

Mar. 28, 2019    (KR) .................. 10-2019-0035683

(51) Int. Cl.
| | | |
|---|---|---|
| *C12P 19/32* | (2006.01) | |
| *C12N 9/10* | (2006.01) | |
| *C12N 15/77* | (2006.01) | |
| *C12N 15/52* | (2006.01) | |

(52) U.S. Cl.
CPC ............ *C12P 19/32* (2013.01); *C12N 9/1077* (2013.01); *C12N 15/52* (2013.01); *C12N 15/77* (2013.01); *C12Y 204/02014* (2013.01)

(58) Field of Classification Search
None
See application file for complete search history.

(56) References Cited

FOREIGN PATENT DOCUMENTS

| | | |
|---|---|---|
| KR | 1020050043979 A | 5/2005 |
| KR | 1020050056670 A | 6/2005 |
| KR | 1020070056491 A | 6/2007 |
| KR | 1020080025355 A | 3/2008 |
| KR | 1020100109732 A | 10/2010 |
| KR | 101904675 B1 | 9/2018 |
| KR | 101950141 B1 | 2/2019 |
| WO | 2008/033001 A1 | 3/2008 |

OTHER PUBLICATIONS

Database Patric [Online] Virginia Tech Cyberinfrastructure Division; Apr. 6, 2016 "Amidophosphoribosyltransferase (EC 2.4.2.14)" XP002801462 retrieved from Bacterial Bioinformatics Resource Center, Database Accession No. fig | 1077974.3.peg.3565 (1 page).
Supplementary European Search Report corresponding to EP Application No. EP 19 76 2700, 7 pages, dated Jan. 11, 2021.
GenBank: KQB83970.1, Amidophosphoribosyltransferase precursor [Corynebacterium lowii] (2 pages) (Oct. 23, 2015).
GenBank: STC68793.1, amidophosphoribosyltransferase [Corynebacterium pilosum] (1 page) (Jul. 30, 2018).
Examination report No. 1 for standard patent application, corresponding to Australian Application No. 2019226146, 17 pages, dated Feb. 9, 2021.

*Primary Examiner* — Suzanne M Noakes
(74) *Attorney, Agent, or Firm* — Seed IP Law Group LLP

(57) ABSTRACT

Provided are a variant phosphoribosylpyrophosphate amidotransferase, a microorganism including the same, and a method of preparing a purine nucleotide using the same.

8 Claims, No Drawings

Specification includes a Sequence Listing.

SEQUENCE LISTING

```
<160> NUMBER OF SEQ ID NOS: 24

<210> SEQ ID NO 1
<211> LENGTH: 1500
<212> TYPE: DNA
<213> ORGANISM: Unknown
<220> FEATURE:
<223> OTHER INFORMATION: purF

<400> SEQUENCE: 1
gtggtgaaca ctactttccc cagcgacgtg aatttagatg accaaggcga gcaagaaccc      60
cgcgaagagt gcggtgtctt tggcgtctgg gctcctggtg aagatgttgc gacactgacc     120
tactttggtc tgttcgcatt gcagcatcgt gggcaggaag ctgcaggtat cggcgtcggt     180
gatggagacc gcctcgttgt cttcaaagac atgggcttgg tctcgaatat tttcgatgag     240
tccattttaa attccctcca tggctccgtg ggcgtggggc atacgcgcta ctcgactgcc     300
ggtggcaaag agtggtcgaa tgtccagccg atgtttaata ccacctcaaa tggggtagac     360
atcgctttgt gccacaacgg caacttggtg aactaccaag aactgcgcga tgaagcagta     420
```

```
gctctgggac tttaccgaga gaatgaaaaa tccctgtcgg attccatgat catgacagct    480
ttgctggcgc acggagtcgg ggaaggcaac tctgtctttg acgccgctaa gcaactgctg    540
ccaagcatca aaggcgcttt tgcttgacc tttaccgatg gcaagacctt gtacgccgcg    600
cgtgacccgc acggtgtacg ccccttggtc attggccgct ggcgcaaggc tgggttgtt     660 gcttccgaaa cctgtgcgct ggatatcgtg ggcgcacagt ttatccgtga ggtagagccc    720
ggtgaactta tctctgtcaa tgaggcagga atccacagcg aaaaattcgc tgagccgaag    780
cgccagggct gcgtctttga atacgtctac ttggcacgtc agacaccgt gatcaaaggc     840 cgcaacgttc acgcgacgcg cgtggatatt ggtcgcgcac ttgcgaaatc tcaccctgcg    900
ccagaagctg acatggtcat ccccgtgcca gaatccggaa accggcagc tgttggctac     960 gcccgggaat cgggcctgac atttgcgcac ggcttggtca aaacgcta cgtgggtcga     1020 accttcattc agcccaccca gaccttgcgc cagctgggta ttcgcctcaa gctcaacccc    1080
ctgcgcgagg tcatcgaggg caagtcactc gttgttgtag atgactctat tgtccgcggc    1140
aacacccaac gcgcgctggt gcgcatgctg cgtgaagcag gcgctgctga agtgcacgtg    1200
cgcattgctt caccgccagt caaatggcct tgtttctacg gcattgactt cgcctcgcct    1260
ggtgaattga ttgctaatat caagccttct gatgatcctc aggtagtaac cgatgcagtg    1320
tgcgaagcta tcggagcaga ctctttaggg tttgtatctg tagatgagat ggttgaggca    1380
acgcaccaac ctatcaattc cttgtgtacc gcttgctttg atggcaacta cgaactcgga    1440
cttccgaccg ctaaccccaa tgctgacgct gtgcgaactt tgctcagcca aagaactga    1500
```

<210> SEQ ID NO 2
<211> LENGTH: 499
<212> TYPE: PRT
<213> ORGANISM: Unknown
<220> FEATURE:
<223> OTHER INFORMATION: purF

<400> SEQUENCE: 2

```
Met Val Asn Thr Thr Phe Pro Ser Asp Val Asn Leu Asp Asp Gln Gly
1               5                   10                  15

Glu Gln Glu Pro Arg Glu Glu Cys Gly Val Phe Gly Val Trp Ala Pro
            20                  25                  30

Gly Glu Asp Val Ala Thr Leu Thr Tyr Phe Gly Leu Phe Ala Leu Gln
        35                  40                  45

His Arg Gly Gln Glu Ala Ala Gly Ile Gly Val Gly Asp Gly Asp Arg
    50                  55                  60

Leu Val Val Phe Lys Asp Met Gly Leu Val Ser Asn Ile Phe Asp Glu
65                  70                  75                  80

Ser Ile Leu Asn Ser Leu His Gly Ser Val Gly Val Gly His Thr Arg
                85                  90                  95

Tyr Ser Thr Ala Gly Gly Lys Glu Trp Ser Asn Val Gln Pro Met Phe
            100                 105                 110

Asn Thr Thr Ser Asn Gly Val Asp Ile Ala Leu Cys His Asn Gly Asn
        115                 120                 125

Leu Val Asn Tyr Gln Glu Leu Arg Asp Glu Ala Val Ala Leu Gly Leu
    130                 135                 140

Tyr Arg Glu Asn Glu Lys Ser Leu Ser Asp Ser Met Ile Met Thr Ala
145                 150                 155                 160

Leu Leu Ala His Gly Val Gly Glu Gly Asn Ser Val Phe Asp Ala Ala
                165                 170                 175
```

```
Lys Gln Leu Leu Pro Ser Ile Lys Gly Ala Phe Cys Leu Thr Phe Thr
                180                 185                 190

Asp Gly Lys Thr Leu Tyr Ala Ala Arg Asp Pro His Gly Val Arg Pro
            195                 200                 205

Leu Val Ile Gly Arg Leu Ala Gln Gly Trp Val Val Ala Ser Glu Thr
210                 215                 220

Cys Ala Leu Asp Ile Val Gly Ala Gln Phe Ile Arg Glu Val Glu Pro
225                 230                 235                 240

Gly Glu Leu Ile Ser Val Asn Glu Ala Gly Ile His Ser Glu Lys Phe
                245                 250                 255

Ala Glu Pro Lys Arg Gln Gly Cys Val Phe Glu Tyr Val Tyr Leu Ala
            260                 265                 270

Arg Pro Asp Thr Val Ile Lys Gly Arg Asn Val His Ala Thr Arg Val
        275                 280                 285

Asp Ile Gly Arg Ala Leu Ala Lys Ser His Pro Ala Pro Glu Ala Asp
    290                 295                 300

Met Val Ile Pro Val Pro Glu Ser Gly Asn Pro Ala Ala Val Gly Tyr
305                 310                 315                 320

Ala Arg Glu Ser Gly Leu Thr Phe Ala His Gly Leu Val Lys Asn Ala
                325                 330                 335

Tyr Val Gly Arg Thr Phe Ile Gln Pro Thr Gln Thr Leu Arg Gln Leu
            340                 345                 350

Gly Ile Arg Leu Lys Leu Asn Pro Leu Arg Glu Val Ile Glu Gly Lys
        355                 360                 365

Ser Leu Val Val Asp Asp Ser Ile Val Arg Gly Asn Thr Gln Arg
    370                 375                 380

Ala Leu Val Arg Met Leu Arg Glu Ala Gly Ala Ala Glu Val His Val
385                 390                 395                 400

Arg Ile Ala Ser Pro Pro Val Lys Trp Pro Cys Phe Tyr Gly Ile Asp
                405                 410                 415

Phe Ala Ser Pro Gly Glu Leu Ile Ala Asn Ile Lys Pro Ser Asp Asp
            420                 425                 430

Pro Gln Val Val Thr Asp Ala Val Cys Glu Ala Ile Gly Ala Asp Ser
        435                 440                 445

Leu Gly Phe Val Ser Val Asp Glu Met Val Glu Ala Thr His Gln Pro
    450                 455                 460

Ile Asn Ser Leu Cys Thr Ala Cys Phe Asp Gly Asn Tyr Glu Leu Gly
465                 470                 475                 480

Leu Pro Thr Ala Asn Pro Asn Ala Asp Ala Val Arg Thr Leu Leu Ser
                485                 490                 495

Gln Lys Asn

<210> SEQ ID NO 3
<211> LENGTH: 29
<212> TYPE: DNA
<213> ORGANISM: Artificial Sequence
<220> FEATURE:
<223> OTHER INFORMATION: purA alt-1

<400> SEQUENCE: 3
gctctagagg ccacgatgcc cggagcatc                                    29

<210> SEQ ID NO 4
<211> LENGTH: 37
<212> TYPE: DNA
<213> ORGANISM: Artificial Sequence
```

```
<220> FEATURE:
<223> OTHER INFORMATION: purA alt-2

<400> SEQUENCE: 4
taacgatagc tgccaaggtt attcacttcc tagattt                              37

<210> SEQ ID NO 5
<211> LENGTH: 37
<212> TYPE: DNA
<213> ORGANISM: Artificial Sequence
<220> FEATURE:
<223> OTHER INFORMATION: purA alt-3

<400> SEQUENCE: 5
aggaagtgaa taaccttggc agctatcgtt atcgtcg                              37

<210> SEQ ID NO 6
<211> LENGTH: 29
<212> TYPE: DNA
<213> ORGANISM: Artificial Sequence
<220> FEATURE:
<223> OTHER INFORMATION: purA alt-4

<400> SEQUENCE: 6
gctctagagg tcacgaatgg gtaggtgcc                                       29

<210> SEQ ID NO 7
<211> LENGTH: 29
<212> TYPE: DNA
<213> ORGANISM: Artificial Sequence
<220> FEATURE:
<223> OTHER INFORMATION: guaB alt-1

<400> SEQUENCE: 7
gctctagact acgacaacac ggtgcctaa                                       29

<210> SEQ ID NO 8
<211> LENGTH: 37
<212> TYPE: DNA
<213> ORGANISM: Artificial Sequence
<220> FEATURE:
<223> OTHER INFORMATION: guaB alt-2

<400> SEQUENCE: 8
cacgattttc ggtcaatacg ggtcttctcc ttcgcac                              37

<210> SEQ ID NO 9
<211> LENGTH: 36
<212> TYPE: DNA
<213> ORGANISM: Artificial Sequence
<220> FEATURE:
<223> OTHER INFORMATION: guaB alt-3

<400> SEQUENCE: 9
aggagaagac ccgtattgac cgaaaatcgt gtttct                               36

<210> SEQ ID NO 10
<211> LENGTH: 29
<212> TYPE: DNA
<213> ORGANISM: Artificial Sequence
<220> FEATURE:
<223> OTHER INFORMATION: guaB alt-4

<400> SEQUENCE: 10
gctctagaat cgacaagcaa gcctgcacg                                       29
```

```
<210> SEQ ID NO 11
<211> LENGTH: 20
<212> TYPE: DNA
<213> ORGANISM: Artificial Sequence
<220> FEATURE:
<223> OTHER INFORMATION: purF tempF

<400> SEQUENCE: 11
aagttgatgc ttcaggcaca                                              20

<210> SEQ ID NO 12
<211> LENGTH: 20
<212> TYPE: DNA
<213> ORGANISM: Artificial Sequence
<220> FEATURE:
<223> OTHER INFORMATION: purF tempR

<400> SEQUENCE: 12
tgcaaggatt ggctctttgt                                              20

<210> SEQ ID NO 13
<211> LENGTH: 19
<212> TYPE: DNA
<213> ORGANISM: Artificial Sequence
<220> FEATURE:
<223> OTHER INFORMATION: purF lib F

<400> SEQUENCE: 13
acacgagata gcccagtgg                                               19

<210> SEQ ID NO 14
<211> LENGTH: 20
<212> TYPE: DNA
<213> ORGANISM: Artificial Sequence
<220> FEATURE:
<223> OTHER INFORMATION: purF lib R

<400> SEQUENCE: 14
tcgtagttgc catcaaagca                                              20

<210> SEQ ID NO 15
<211> LENGTH: 19
<212> TYPE: DNA
<213> ORGANISM: Artificial Sequence
<220> FEATURE:
<223> OTHER INFORMATION: purF seq F

<400> SEQUENCE: 15
acacgagata gcccagtgg                                               19

<210> SEQ ID NO 16
<211> LENGTH: 21
<212> TYPE: DNA
<213> ORGANISM: Artificial Sequence
<220> FEATURE:
<223> OTHER INFORMATION: purF seq R

<400> SEQUENCE: 16
accaagtcat cgacgcacat t                                            21

<210> SEQ ID NO 17
<211> LENGTH: 30
<212> TYPE: DNA
<213> ORGANISM: Artificial Sequence
<220> FEATURE:
<223> OTHER INFORMATION: purF V2M 1F
```

<400> SEQUENCE: 17
gggtctagaa gtactgaccc gaccactgca                                              30

<210> SEQ ID NO 18
<211> LENGTH: 27
<212> TYPE: DNA
<213> ORGANISM: Artificial Sequence
<220> FEATURE:
<223> OTHER INFORMATION: purF V2M 1R

<400> SEQUENCE: 18
tggggaaagt agtgttcatc acgacgc                                                 27

<210> SEQ ID NO 19
<211> LENGTH: 27
<212> TYPE: DNA
<213> ORGANISM: Artificial Sequence
<220> FEATURE:
<223> OTHER INFORMATION: purF V2M 2F

<400> SEQUENCE: 19
tagtagaatc agcgtcgtga tgaacac                                                 27

<210> SEQ ID NO 20
<211> LENGTH: 30
<212> TYPE: DNA
<213> ORGANISM: Artificial Sequence
<220> FEATURE:
<223> OTHER INFORMATION: purF V2M 2R

<400> SEQUENCE: 20
gggtctagat ggattcctgc ctcattgaca                                              30

<210> SEQ ID NO 21
<211> LENGTH: 30
<212> TYPE: DNA
<213> ORGANISM: Artificial Sequence
<220> FEATURE:
<223> OTHER INFORMATION: purF G445R 1F

<400> SEQUENCE: 21
gggtctagac cgatggcaag accttgtacg                                              30

<210> SEQ ID NO 22
<211> LENGTH: 31
<212> TYPE: DNA
<213> ORGANISM: Artificial Sequence
<220> FEATURE:
<223> OTHER INFORMATION: purF G445R 1R

<400> SEQUENCE: 22
caaaccctaa agagtctgct ctgatagctt c                                            31

<210> SEQ ID NO 23
<211> LENGTH: 30
<212> TYPE: DNA
<213> ORGANISM: Artificial Sequence
<220> FEATURE:
<223> OTHER INFORMATION: purF G445R 2F

<400> SEQUENCE: 23
cagtgtgcga agctatcaga gcagactctt                                              30

<210> SEQ ID NO 24

```
<211> LENGTH: 32
<212> TYPE: DNA
<213> ORGANISM: Artificial Sequence
<220> FEATURE:
<223> OTHER INFORMATION: purF G445R 2R

<400> SEQUENCE: 24
gggtctagac aaggtcatcg atgtagccat cg                                      32
```

VARIANT PHOSPHORIBOSYLPYROPHOSPHATE AMIDOTRANSFERASE AND METHOD OF PREPARING PURINE NUCLEOTIDE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_453USPC_SEQUENCE_LISTING.txt. The text file is 9.9 KB, was created on Sep. 3, 2019, and is being submitted electronically via EFS-Web.

TECHNICAL FIELD

The present disclosure relates to a variant phosphoribosylpyrophosphate amidotransferase, a microorganism including the same, a method of preparing a purine nucleotide using the same, a composition for producing a purine nucleotide, a method for increasing the production of a purine nucleotide, or use of the variant phosphoribosylpyrophosphate amidotransferase.

BACKGROUND ART

5'-Inosinic acid (5'-inosine monophosphate; hereinafter referred to as IMP), which is a nucleotide-based material, is an intermediate material of the metabolic system of nucleic acid biosynthesis, and is used in a variety of fields, such as medical products and medical applications. IMP is a material that is widely used as a food seasoning additive or for foods, together with 5'-guanylic acid (5'-guanine monophosphate; hereinafter referred to as GMP). IMP itself is known to have a beef flavor, and is known to enhance the flavor of monosodium glutamic acid (MSG), like GMP. Therefore, IMP has received much attention as a nucleotide-based taste seasoning.

Methods of preparing IMP include a method of enzymatically degrading ribonucleic acids which are extracted from yeast cells, a method of chemically phosphorylating inosine which is produced by fermentation (Agri. Biol. Chem., 36, 1511(1972), etc.), a method of culturing a microorganism capable of directly producing IMP and then recovering IMP in a culture thereof, etc. Among these methods, the most commonly used method is the method of using a microorganism capable of directly producing IMP.

Further, methods of preparing GMP include a method of converting 5'-xanthylic acid (5'-xanthosine monophosphate; hereinafter referred to as XMP) produced by microbial fermentation into GMP using a coryneform microorganism, and a method of converting XMP produced by microbial fermentation into GMP using *Escherichia coli*. According to the methods, when XMP is produced and then converted into GMP, it is necessary to enhance productivity of XMP, which is a precursor of the conversion reaction during microbial fermentation, and it is required to prevent loss of GMP which has already been produced throughout the conversion reaction as well as produced XMP.

Meanwhile, enzymes in their natural state do not always exhibit optimal properties in terms of activity, stability, substrate specificity for optical isomers, etc., which are required in industrial applications. Therefore, various attempts have been made to improve enzymes through variations of their amino acid sequences, etc. such that they become suitable for the intended use. Of these, rational design and site-directed mutagenesis of enzymes have been applied in order to improve enzyme functions. However, in many cases, there is a disadvantage in that information on the structure of a target enzyme is not sufficient, or the structure-function relationship is not clear, and therefore, the methods cannot be effectively applied. In this regard, it is reported that the enzyme improvement is attempted by way of a directed evolution method of screening for an enzyme of a desired trait from a mutant enzyme library which is constructed through random mutagenesis of the enzyme gene, leading to improvement of its activity.

DISCLOSURE

Technical Problem

The present inventors have conducted extensive studies to produce a purine nucleotide with a high yield by a method of producing the purine nucleotide through microbial fermentation, and they identified a variant of a protein having a higher purine nucleotide productivity, thereby completing the present disclosure.

Technical Solution

An object of the present disclosure is to provide a variant phosphoribosylpyrophosphate amidotransferase.

Another object of the present disclosure is to provide a polynucleotide encoding the variant phosphoribosylpyrophosphate amidotransferase.

Still another object of the present disclosure is to provide a vector including the polynucleotide.

Still another object of the present disclosure is to provide a microorganism producing a purine nucleotide, the microorganism including the variant phosphoribosylpyrophosphate amidotransferase or the vector.

Still another object of the present disclosure is to provide a method of preparing a purine nucleotide, the method including the step of culturing a microorganism of the genus *Corynebacterium* in a medium.

Still another object of the present disclosure is to provide a composition for producing a purine nucleotide, comprising the variant phosphoribosylpyrophosphate amidotransferase of the present disclosure.

Still another object of the present disclosure is to provide a method for increasing the production of a purine nucleotide, comprising the variant phosphoribosylpyrophosphate amidotransferase of the present disclosure.

Still another object of the present disclosure is to provide use of the variant phosphoribosylpyrophosphate amidotransferase for the production of a purine nucleotide.

Still another object of the present disclosure is to provide use of the polynucleotide for the production of a purine nucleotide.

Still another object of the present disclosure is to provide use of the microorganism of the genus *Corynebacterium* for the production of a purine nucleotide.

Advantageous Effects

When a variant phosphoribosylpyrophosphate amidotransferase of the present disclosure is used to culture a microorganism of the genus *Corynebacterium*, it is possible to produce a purine nucleotide with a high yield. Further, the prepared purine nucleotide may be applied not only to animal feeds or animal feed additives but also to various products such as human food or food additives, seasonings, medicines, etc.

BEST MODE

A detailed description is as follows. Meanwhile, respective descriptions and embodiments disclosed in this application may also be applied to other descriptions and embodiments. That is, all combinations of various elements disclosed in this application fall within the scope of the present application. Further, the scope of the present application is not limited by the specific description described below.

In order to achieve the above objects, an aspect of the present disclosure provides a variant phosphoribosylpyrophosphate amidotransferase having a polypeptide including substitution of one or more amino acids in an amino acid sequence of SEQ ID NO: 2. Specifically, the present disclosure provides the variant phosphoribosylpyrophosphate amidotransferase having the polypeptide including substitution of one or more amino acids in the amino acid sequence of SEQ ID NO: 2, wherein the amino acid substitution includes substitution of an amino acid at position 2 and/or substitution of an amino acid at position 445 from the N-terminus of SEQ ID NO: 2.

Another aspect of the present disclosure provides a variant phosphoribosylpyrophosphate amidotransferase, wherein i) methionine is substituted for the amino acid at position 2, ii) arginine is substituted for the amino acid at position 455, or iii) methionine is substituted for the amino acid at position 2 and arginine is substituted for the amino acid at position 455 from the N-terminus of the amino acid sequence of SEQ ID NO: 2.

As used herein, the term "phosphoribosylpyrophosphate amidotransferase" refers to an enzyme that has an important role in purine biosynthesis. With respect to the objects of the present disclosure, the enzyme refers to a protein involved in production of purine nucleotides.

In the present disclosure, SEQ ID NO: 2 refers to an amino acid sequence having phosphoribosylpyrophosphate amidotransferase activity. Specifically, SEQ ID NO: 2 is a sequence of a protein having activity of phosphoribosylpyrophosphate amidotransferase, which is encoded by purF gene. The amino acid sequence of SEQ ID NO: 2 may be obtained from NCBI GenBank, which is a public database. For example, although not limited thereto, the amino acid sequence of SEQ ID NO: 2 may be derived from the genus *Corynebacterium* (*Corynebacterium* sp.), and may include any sequence having the same activity as that of the above amino acid sequence without limitation. Further, the scope of the amino acid sequence of SEQ ID NO: 2 may include an amino acid sequence having activity of phosphoribosylpyrophosphate amidotransferase of SEQ ID NO: 2 or an amino acid sequence having 80% or more homology or identity thereto, but is not limited thereto. Specifically, the amino acid sequence may include the amino acid sequence of SEQ ID NO: 2 or an amino acid sequence having at least 80%, 85%, 90%, 95%, 96%, 97%, 98%, or 99% or more homology or identity to the amino acid sequence of SEQ ID NO: 2. The amino acid sequence having homology or identity may be those excluding a sequence having 100% identity from the above range, or may be a sequence having less than 100% identity. Further, it is apparent that a protein having an amino acid sequence having deletion, modification, substitution, or addition of some amino acids also falls within the scope of the present invention, as long as it has the homology or identity and exhibits efficacy corresponding to that of the above protein.

As used herein, the term "variant phosphoribosylpyrophosphate amidotransferase" may be used interchangeably with a variant polypeptide having purine nucleotide productivity, a purine nucleotide-producing variant polypeptide, a variant polypeptide producing a purine nucleotide, a variant polypeptide having phosphoribosylpyrophosphate amidotransferase activity, a phosphoribosylpyrophosphate amidotransferase variant, etc.

The variant phosphoribosylpyrophosphate amidotransferase may include variation(s) at position 2 and/or at position 445 from the N-terminus in the amino acid sequence of SEQ ID NO: 2. The variant phosphoribosylpyrophosphate amidotransferase may have substitution of another amino acid (s) for the amino acid(s) at position 2 and/or at position 445 in the amino acid sequence of SEQ ID NO: 2 and enhanced activity, as compared with those including the amino acid sequence of SEQ ID NO: 2 or a non-modified phosphoribosylpyrophosphate amidotransferase derived from the wild-type microorganism. Such a variant phosphoribosylpyrophosphate amidotransferase means those having variation of the amino acid at position 2 or at position 445 from the N-terminus of the SEQ ID NO: 2 and/or an amino acid sequence having at least 80%, 85%, 90%, 95%, 96%, 97%, 98%, or 99% or more homology or identity to SEQ ID NO: 2, as described above.

For example, the variant phosphoribosylpyrophosphate amidotransferase may have i) substitution of methionine for the amino acid at position 2, ii) substitution of arginine for the amino acid at position 445, or iii) substitution of methionine for the amino acid at position 2 and substitution of arginine for the amino acid at position 445 in the amino acid sequence of SEQ ID NO: 2, and may have enhanced phosphoribosylpyrophosphate amidotransferase activity, as compared with the polypeptide including the amino acid sequence of SEQ ID NO: 2, but is not limited thereto.

With respect to the objects of the present disclosure, a microorganism including the variant phosphoribosylpyrophosphate amidotransferase has higher purine nucleotide productivity than a wild-type microorganism, a microorganism including the wild-type phosphoribosylpyrophosphate amidotransferase, or a microorganism including no variant phosphoribosylpyrophosphate amidotransferase. The present disclosure is of significance in that the purine nucleotide production by microorganisms may be increased by using the variant phosphoribosylpyrophosphate amidotransferase of the present disclosure, whereas the wild-type strain of the genus *Corynebacterium* is not able to produce purine nucleotides or, even though it produces purine nucleotides, it is able to produce trace amounts thereof.

Specifically, the variant phosphoribosylpyrophosphate amidotransferase may include an amino acid sequence having substitution of another amino acid(s) for the amino acid(s) at position 2 and/or at position 445. Specifically, the variant phosphoribosylpyrophosphate amidotransferase may be composed of a polypeptide including i) substitution of methionine for the amino acid at position 2, ii) substitution of arginine for the amino acid at position 445, or iii) substitution of methionine for the amino acid at position 2 and substitution of arginine for the amino acid at position 445 from the N-terminus in the amino acid sequence of SEQ ID NO: 2. Further, the variant phosphoribosylpyrophosphate amidotransferase may include an amino acid sequence where another amino acid(s) is/are substituted for the amino acid(s) at position 2 and/or at position 445 from the N-terminus in the amino acid sequence of SEQ ID NO: 2, or an amino acid sequence having 80% or more homology or identity thereto, but is not limited thereto. Specifically, the variant phosphoribosylpyrophosphate amidotransferase of the present disclosure may include a polypeptide having at least 80%, 85%, 90%, 95%, 96%, 97%, 98%, or 99% or more homology or identity to the amino acid sequence having substitution of methionine for the amino acid at position 2 or substitution of arginine for the amino acid at position 445 in the amino acid sequence of SEQ ID NO: 2. Further, it is apparent that a protein having an amino acid sequence having deletion, modification, substitution, or addition of other amino acid sequences than the amino acid sequence at positions 2 and/or 445 also falls within the scope of the present invention, as long as it has the homology or identity and exhibits efficacy corresponding to that of the above protein.

In other words, even though the present disclosure describes a 'protein or polypeptide having an amino acid sequence represented by a particular SEQ ID NO:', it is apparent that a protein having an amino acid sequence having deletion, alteration, substitution, conservative substitution, or addition of some amino acids may also be used in the present disclosure, as long as it has activity identical or corresponding to that of the polypeptide having the amino acid sequence of the corresponding SEQ ID NO:. For example, as long as a protein has the activity identical or corresponding to that of the variant phosphoribosylpyrophosphate amidotransferase, it does not exclude sequence addition, naturally occurring mutation, silent mutation, or conservative substitution thereof which does not alter the function of the protein, before and after the amino acid sequence. It is apparent that a protein having such a sequence addition or mutation also falls within the scope of the present disclosure.

The "conservative substitution" means replacement of an amino acid with another amino acid having similar structural and/or chemical properties. This amino acid substitution may be generally made on the basis of similarity in polarity, charge, solubility, hydrophobicity, hydrophilicity, and/or amphipathic nature. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan.

Therefore, in the present disclosure, the "variant" may further include conservative substitution and/or modification of one or more amino acids in 'a protein or polypeptide having an amino acid sequence represented by a particular SEQ ID NO:'. For example, certain variants may include variants in which one or more portions, such as a N-terminal leader sequence or transmembrane domain, have been removed. Another variant may include variants in which a portion has been removed from the N- and/or C-terminus of the mature protein. The variant may also include other modifications, including deletion or addition of amino acids, which have minimal effects on properties and a secondary structure of the polypeptide. For example, the polypeptide may be conjugated to a signal (or leader) sequence at the N-terminal end of a protein that co-translationally or post-translationally directs transfer of the protein. The polypeptide may also be conjugated to another sequence or a linker for ease of identification, purification, or synthesis of the polypeptide. The term "variant" may be used interchangeably with modification, modified protein, modified polypeptide, mutant, mutein, divergent, etc., and any term may be used without limitation, as long as it is used in a sense of being modified.

Homology and identity mean a degree of relatedness between two given amino acid sequences or nucleotide sequences, and may be expressed as a percentage. The terms homology and identity may often be used interchangeably with each other.

Sequence homology or identity of a conserved polynucleotide or polypeptide may be determined by a standard alignment algorithm used with default gap penalties established by a program to be used. Substantially, homologous or identical sequences may hybridize under moderately or highly stringent conditions along their entire sequence or at least about 50%, about 60%, about 70%, about 80%, or about 90% of the entire length. With regard to the polynucleotides to be hybridized, polynucleotides including a degenerate codon instead of a codon may also be contemplated.

In general, as codon defines which amino acid to be encoded, a codon is formed by pairing three nucleotide sequences. There are more kinds of codon compared to that of amino acid to be encoded, and the kind of amino acid to be produced differs according to the combination of codons. Translation starts from an initiation codon and the first amino acid to be translated may be fMet. Generally, translation proceeds by transporting fMET for the mRNA codon corresponding to the atg sequence of DNA. However, translation can proceed by transporting fMET when the first DNA of mRNA ORF (open reading frame) is gtg or ttg. That is, the initiation codon may be atg, gtg, or ttg.

Whether any two polynucleotide or polypeptide sequences have homology, similarity, or identity may be determined by, for example, a known computer algorithm such as the "FASTA" program using default parameters as in Pearson et al. (1988)[Proc. Natl. Acad. Sci. USA 85]: 2444, and alternatively, determined by using the Needleman-Wunsch algorithm (Needleman and Wunsch, 1970, J. Mol. Biol. 48: 443-453) as implemented in the Needleman program of the EMBOSS package (EMBOSS: The European Molecular Biology Open Software Suite, Rice et al., 2000, Trends Genet. 16: 276-277) (version 5.0.0 or later) (including GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, homology, similarity, or identity may be determined using BLAST, or ClustalW of the National Center for Biotechnology Information.

Homology, similarity, or identity of polynucleotides or polypeptides may be determined by comparing sequence information using a GAP computer program, for example, Needleman et al. (1970), J Mol Biol. 48: 443, as disclosed in Smith and Waterman, Adv. Appl. Math (1981) 2:482. Briefly, the GAP program defines similarity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) Nucl. Acids Res. 14: 6745, as described by Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap (or gap open penalty 10, gap extension penalty 0.5); and (3) no penalty for end gaps. Therefore, the term "homology" or "identity", as used herein, represents relevance between sequences.

Due to codon degeneracy, it is apparent that a polynucleotide to be translated into the variant polypeptide having substitution of another amino acid(s) for the amino acid(s) at position 2 and/or at position 445 from the N-terminus of the amino acid sequence of SEQ ID NO: 2, or a variant polypeptide having homology or identity thereto may also be included. Further, by hybridization under stringent conditions with a probe prepared from a known gene sequence, for example, a sequence complementary to all or part of the nucleotide sequence, a polynucleotide sequence encoding the variant phosphoribosylpyrophosphate amidotransferase including the amino acid sequence wherein i) substitution of methionine for the amino acid at position 2, ii) substitution of arginine for the amino acid at position 445, or iii) substitution of methionine for the amino acid at position 2 and substitution of arginine for the amino acid at position 445 in the amino acid sequence of SEQ ID NO: 2 may be included without limitation.

As used herein, the term "polynucleotide" refers to a DNA or RNA strand having more than a certain length as a nucleotide polymer, which is a long chain of nucleotide monomers connected by covalent bonds, and more specifically, to a polynucleotide fragment encoding a polypeptide.

The polynucleotide encoding the variant phosphoribosylpyrophosphate amidotransferase of the present disclosure may include any polynucleotide sequence without limitation, as long as it encodes the variant polypeptide having phosphoribosylpyrophosphate amidotransferase activity of the present disclosure. In the present disclosure, a gene encoding the amino acid sequence of phosphoribosylpyrophosphate amidotransferase is purF gene, and specifically, the gene may be derived from *Corynebacterium stationis*, but is not limited thereto.

Specifically, due to codon degeneracy or by considering codons preferred by a microorganism in which the polypeptide is allowed to express, various modifications may be made in the coding region of the polynucleotide of the present disclosure within the scope that does not change the amino acid sequence of the polypeptide. Any polynucleotide sequence may be included without limitation as long as it encodes the variant phosphoribosylpyrophosphate amidotransferase having substitution of another amino acid for the amino acid at position 2 or at position 445 in the amino acid sequence of SEQ ID NO: 2. For example, the polynucleotide of the present disclosure may include a sequence having some modified sequence in SEQ ID NO: 1, but is not limited thereto.

Further, by hybridization under stringent conditions with a probe prepared from a known gene sequence, for example, a sequence complementary to all or part of the nucleotide sequence, a sequence encoding a protein having activity of the variant phosphoribosylpyrophosphate amidotransferase having substitution of another amino acid for the amino acid at position 2 or at position 445 in the amino acid sequence of SEQ ID NO: 2 may be included without limitation. The "stringent conditions" mean conditions that permit specific hybridization between polynucleotides. Such conditions are described in detail in a literature (e.g., J. Sambrook et al., supra). The stringent conditions may include conditions under which genes having high homology or identity, for instance, genes having 40% or more, specifically 85% or more, 90% or more, more specifically 95% or more, still more specifically 97% or more, particularly specifically 99% or more homology or identity are able to hybridize to each other, and genes having lower homology or identity are not able to hybridize to each other, or conditions which are common washing conditions for Southern hybridization, e.g., a salt concentration and a temperature corresponding to 60° C., 1×SSC, 0.1% SDS, specifically 60° C., 0.1×SSC, 0.1% SDS, more specifically 68° C., 0.1×SSC, 0.1% SDS, once, specifically, twice or three times.

Hybridization requires that two nucleic acids have complementary sequences, although mismatches between bases are possible depending on stringency of hybridization. The term "complementary" is used to describe the relationship between nucleotide bases that are able to hybridize to one another. For example, with respect to DNA, adenosine is complementary to thymine and cytosine is complementary to guanine. Accordingly, the present disclosure may also include isolated nucleic acid fragments complementary to the complete sequences as well as substantially similar nucleic acid sequences.

Specifically, a polynucleotide having homology or identity may be detected by hybridization conditions including a hybridization step at $T_m$ of 55° C. and by utilizing the above-described conditions. Further, the $T_m$ value may be 60° C., 63° C., or 65° C., but is not limited thereto, and may be properly controlled by those skilled in the art according to the purpose.

The appropriate stringency for hybridizing polynucleotides depends on the length of the polynucleotides and the degree of complementation, and variables are well known in the art (see Sambrook et al., supra, 9.50-9.51, 11.7-11.8).

In the present disclosure, the gene encoding the amino acid sequence of the variant phosphoribosylpyrophosphate amidotransferase is purF gene, and a polynucleotide encoding the same is the same as described above.

In the present disclosure, the polynucleotide encoding the variant phosphoribosylpyrophosphate amidotransferase is also the same as described above.

Still another aspect of the present disclosure provides a polynucleotide encoding the variant phosphoribosylpyrophosphate amidotransferase, or a vector including the polynucleotide.

As used herein, the term "vector" means a DNA construct containing the nucleotide sequence of the polynucleotide encoding the desired polypeptide which is operably linked to a suitable control sequence such that the desired polypeptide is expressed in a suitable host. The control sequences may include a promoter to direct transcription, a certain operator sequence to control such transcription, a sequence encoding a suitable ribosome-binding site on mRNA, and a sequence to control termination of transcription and translation. Once transformed into a suitable host, the vector may replicate or function independently of the host genome, or may integrate into the genome itself.

The vector used in the present disclosure may not be particularly limited as long as the vector is replicable in the host cell, and any vector known in the art may be used. Examples of the vector commonly used may include natural or recombinant plasmids, cosmids, viruses, and bacteriophages. For example, as a phage vector or a cosmid vector, pWE15, M13, MBL3, MBL4, IXII, ASHII, APII, t10, t11, Charon4A, Charon21A, etc. may be used, and as a plasmid vector, those based on pBR, pUC, pBluescriptII, pGEM, pTZ, pCL, pET, etc. may be used. Specifically, pDZ, pACYC177, pACYC184, pCL, pECCG117, pUC19, pBR322, pMW118, pCC1BAC vector, etc. may be used.

For example, the polynucleotide encoding the desired polypeptide may be inserted into the chromosome through a vector for chromosomal insertion in a cell. The insertion of the polynucleotide into the chromosome may be performed using any method known in the art, e.g., by homologous recombination, but is not limited thereto. A selection marker for confirming the insertion of the vector into the chromosome may be further included. The selection marker is used for selection of cells transformed with the vector, i.e., in order to confirm whether the desired nucleic acid molecule has been inserted, and markers capable of providing selectable phenotypes such as drug resistance, auxotrophy, resistance to cytotoxic agents, and expression of surface proteins may be used. Under the circumstances where selective agents are treated, only the cells capable of expressing the selection markers can survive or express other phenotypic traits, and thus the transformed cells may be selected.

Still another aspect of the present disclosure provides a microorganism producing a purine nucleotide, the microorganism including the variant phosphoribosylpyrophosphate amidotransferase or the polynucleotide encoding the variant phosphoribosylpyrophosphate amidotransferase. Specifically, the microorganism including the variant phosphoribosylpyrophosphate amidotransferase and/or the polynucleotide encoding the same may be a microorganism prepared by transformation with a vector including the polynucleotide, but is not limited thereto.

As used herein, the term "transformation" refers to a process of introducing a vector which includes a polynucleotide encoding a target protein into a host cell such that the protein encoded by the polynucleotide is able to be expressed in the host cell. It does not matter whether the transformed polynucleotide is inserted into the chromosome of a host cell and located thereon or located outside of the chromosome, as long as the transformed polynucleotide may be expressed in the host cell. Further, the polynucleotide may include DNA and RNA encoding the target protein. The polynucleotide may be introduced in any form, as long as the polynucleotide may be introduced into the host cell and expressed therein. For example, the polynucleotide may be introduced into the host cell in the form of an expression cassette, which is a gene construct including all elements required for its autonomous expression. The expression cassette may include a promoter, a transcription termination signal, a ribosome binding site, and a translation termination signal that may be operably linked to the polynucleotide. The expression cassette may be in the form of an expression vector performing self-replication. In addition, the polynucleotide may be introduced into the host cell as itself to be operably linked to the sequence required for expression in the host cell, but is not limited thereto.

Further, the term "operably linked" refers to a functional linkage between a gene sequence and a promoter sequence which initiates and mediates transcription of the polynucleotide encoding the desired polypeptide of the present disclosure.

The term "microorganism including the variant polypeptide" or "microorganism including the variant phosphoribosylpyrophosphate amidotransferase", as used herein, means a microorganism prepared by providing purine nucleotide productivity for a microorganism having a naturally weak purine nucleotide productivity or a parent strain having no purine nucleotide productivity. The microorganism may be a microorganism expressing the variant phosphoribosylpyrophosphate amidotransferase having the polypeptide including substitution of one or more amino acids in the amino acid sequence of SEQ ID NO: 2, wherein the amino acid substitution may include substitution of methionine for the amino acid at position 2 and/or substitution of arginine for the amino acid at position 445 from the N-terminus of SEQ ID NO: 2. Further, the microorganism may be a microorganism expressing the variant polypeptide, wherein the microorganism has phosphoribosylpyrophosphate amidotransferase activity due to substitution of another amino acid(s) for the amino acid(s) at position 2 and/or at position 445 in the amino acid sequence of SEQ ID NO: 2, but is not limited thereto.

The microorganism may be a cell or a microorganism which may include the polynucleotide encoding the variant phosphoribosylpyrophosphate amidotransferase, or may be transformed with the vector including the polynucleotide encoding the variant phosphoribosylpyrophosphate amidotransferase to express the same, and with respect to the objects of the present disclosure, the host cell or the microorganism may be any microorganism, as long as it includes the variant phosphoribosylpyrophosphate amidotransferase to produce a purine nucleotide.

In the present disclosure, the microorganism producing a purine nucleotide may be used interchangeably with a purine nucleotide-producing microorganism or a microorganism having purine nucleotide productivity.

With respect to the objects of the present disclosure, the "purine nucleotide" means a nucleotide including a purine structure. Examples thereof may include IMP, XMP, or GMP, but are not limited thereto.

Specifically, the term "IMP (5'-inosine monophosphate)" is a nucleic acid-based material composed of the following Chemical Formula 1:

[Chemical Formula 1]

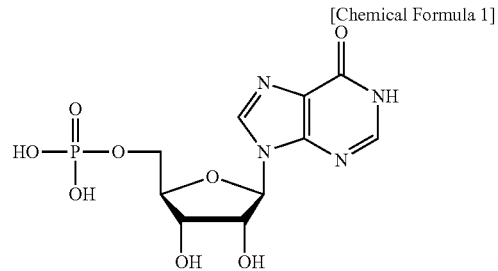

IMP has the IUPAC name of 5'-inosine monophosphate or 5'-inosine acid, and is widely used in foods as a flavor enhancer, together with XMP or GMP.

The term "GMP (5'-guanine monophosphate)" is a nucleic acid-based material composed of the following Chemical Formula 2:

[Chemical Formula 2]

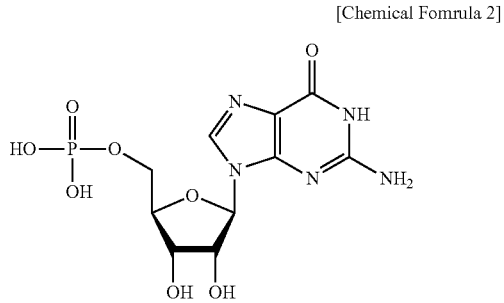

GMP has the IUPAC name of [(2R,3S,4R,5R)-5-(2-amino-6-oxo-1,6-dihydro-9H-purin-9-yl)-3,4-dihydroxytetrahydro-2-furanyl]methyl dihydrogen phosphate, and is also called 5'-guanidylic acid, 5'-guanylic acid, or guanylic acid.

GMP in the form of its salts, such as sodium guanylate, dipotassium guanylate, and calcium guanylate, is widely used as a food additive. When used as an additive together with IMP, GMP exhibits a synergistic effect to enhance flavor. GMP may be prepared by being converted from XMP, but is not limited thereto. As confirmed in one embodiment of the present disclosure, the variant polypeptide of the present disclosure may increase XMP production, and from the increased XMP production, GMP may be converted and its production may be increased. Accordingly, it is apparent that GMP is also included in the scope of the present disclosure.

The term "XMP (5'-xanthosine monophosphate)" is an intermediate material of purine metabolism and is composed of the following Chemical Formula 3. XMP has the IUPAC name of 5'-inosine monophosphate or 5'-xanthylic acid. XMP may be formed from IMP by action of IMP dehydrogenase, or XMP may be converted into GMP by action of GMP synthetase. Further, XMP may be formed from XTP by deoxyribonucleoside triphosphate pyrophosphohydrolase, which is an enzyme having XTPase activity.

[Chemical Formula 3]

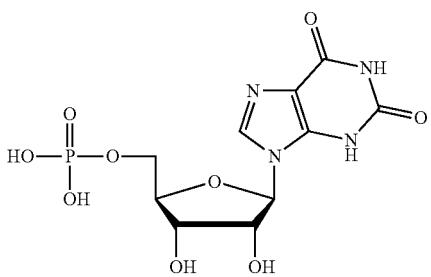

As used herein, the term "microorganism producing a purine nucleotide" may be a microorganism where a genetic modification occurs or activity is enhanced in order to produce the desired purine nucleotide, including all of a wild-type microorganism or a microorganism where a genetic modification naturally or artificially occurs, and the microorganism may be a microorganism where a particular mechanism is weakened or enhanced by insertion of an exogenous gene or by enhancement or inactivation of activity of an endogenous gene. With respect to the objects of the present disclosure, the microorganism producing a purine nucleotide may be characterized in that the microorganism includes the variant phosphoribosylpyrophosphate amidotransferase to have increased productivity of a desired purine nucleotide, and specifically, the microorganism may be a microorganism of the genus Corynebacterium. Specifically, in the present disclosure, the microorganism producing a purine nucleotide or the microorganism having purine nucleotide productivity may be a microorganism where some of the genes involved in the purine nucleotide biosynthesis pathway are enhanced or weakened, or some of the genes involved in the purine nucleotide degradation pathway are enhanced or weakened. For example, the microorganism may be a microorganism where expression of the purA gene encoding adenylosuccinate synthetase is weakened. Additionally, expression of guaB, which is a gene encoding inosine-5'-monophosphate dehydrogenase present in the IMP degradation pathway, may be regulated according to the purine nucleotide. Specifically, when the purine nucleotide is IMP, guaB expression may be weakened, or when the purine nucleotide is XMP or GMP, guaB expression may be enhanced, but its expression is not limited thereto.

As used herein, the term "microorganism of the genus Corynebacterium producing a purine nucleotide" refers to a microorganism of the genus Corynebacterium which has purine nucleotide productivity naturally or due to mutation. Specifically, as used herein, the microorganism of the genus Corynebacterium having purine nucleotide productivity may be a microorganism of the genus Corynebacterium which has improved purine nucleotide productivity due to enhanced activity of the purF gene encoding phosphoribosylpyrophosphate amidotransferase. More specifically, as used herein, the microorganism of the genus Corynebacterium having purine nucleotide productivity refers to a microorganism of the genus Corynebacterium which has improved purine nucleotide productivity due to inclusion of the variant phosphoribosylpyrophosphate amidotransferase or the polynucleotide encoding the same, or due to transformation with the vector including the polynucleotide encoding the variant phosphoribosylpyrophosphate amidotransferase. The 'microorganism of the genus Corynebacterium which has improved purine nucleotide productivity' refers to a microorganism having improved purine nucleotide productivity, as compared with a parent strain before transformation or a non-modified microorganism. The 'non-modified microorganism' refers to a wild-type strain itself, or a microorganism that does not include the variant protein producing purine nucleotide, or a microorganism that is not transformed with the vector including the polynucleotide encoding the variant phosphoribosylpyrophosphate amidotransferase.

As used herein, the "microorganism of the genus Corynebacterium" may be specifically Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis, etc., but is not limited thereto.

Still another aspect of the present disclosure provides a method of preparing a purine nucleotide, the method including the step of culturing the microorganism of the genus Corynebacterium producing a purine nucleotide in a medium. For example, the method of the present disclosure may further include the step of recovering the purine nucleotide from the microorganism or the medium after the step of culturing.

In the method, the step of culturing the microorganism may be performed by, but is not particularly limited to, a known batch culture, continuous culture, fed-batch culture, etc. In this regard, the culture conditions are not particularly limited, but an optimal pH (e.g., pH 5 to pH 9, specifically pH 6 to pH 8, and most specifically pH 6.8) may be adjusted by using a basic compound (e.g., sodium hydroxide, potassium hydroxide, or ammonia) or an acidic compound (e.g., phosphoric acid or sulfuric acid). An aerobic condition may be maintained by adding oxygen or an oxygen-containing gas mixture to the culture. The culture temperature may be maintained at 20° C. to 45° C., and specifically at 25° C. to 40° C., and the culturing may be performed for about 10 hours to about 160 hours, but is not limited thereto. The purine nucleotide produced by the culturing may be secreted into the medium or may remain within the cells.

Moreover, in a culture medium to be used, as a carbon source, sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. may be used individually or in a mixture, but the carbon source is not limited thereto. As a nitrogen source, a nitrogen-containing organic compound (e.g., peptone, yeast extract, meat extract, malt extract, corn steep liquor, soybean flour, and urea), or an inorganic compound (e.g., ammonium sulfate, ammonium chloride, ammonium phosphate, ammonium carbonate and ammonium nitrate), etc. may be used individually or in a mixture, but is not limited thereto. As a phosphorus source, potassium dihydrogen phosphate, dipotassium hydrogen phosphate, sodium-containing salt corresponding thereto, etc. may be used individually or in a mixture, but is not limited thereto. The medium may also include essential growth-promoting materials such as other metal salts (e.g., magnesium sulfate or iron sulfate), amino acids, and vitamins.

A method of recovering the purine nucleotide produced in the culturing step of the present disclosure is to collect the desired purine nucleotide from the culture medium by using an appropriate method known in the art according to the culturing method. For example, centrifugation, filtration, anion exchange chromatography, crystallization, HPLC, etc. may be used, and the desired purine nucleotide may be recovered from the medium or microorganism by using an appropriate method known in the art.

Further, the recovering step may include a purification process. The purification process may be performed by using an appropriate method known in the art. Therefore, the recovered purine nucleotide may be a purified form or a microorganism fermentation liquid including the purine nucleotide (Introduction to Biotechnology and Genetic Engineering, A. J. Nair., 2008).

Still another aspect of the present disclosure provides a composition for producing a purine nucleotide, comprising the variant phosphoribosylpyrophosphate amidotransferase.

The composition for producing a purine nucleotide refers to a composition capable of producing a purine nucleotide by the polynucleotide of the present disclosure. For example, the composition comprises the polynucleotide, and further may comprise, without limitation, a constitution capable of operating the polynucleotide. The polynucleotide may be in a form included in a vector so as to express a gene operably linked to the introduced host cell.

Additionally, the composition may further comprise any suitable excipient conventionally used in a composition for producing a purine nucleotide. Such excipient can be, for example, a preservative, a wetting agent, a dispersing agent, a suspending agent, a buffer, a stabilizing agent, or an isotonic agent, but is not limited thereto.

Still another aspect of the present disclosure provides a method for increasing the production of a purine nucleotide, comprising the step of culturing the variant phosphoribosylpyrophosphate amidotransferase in a microorganism of the genus *Corynebacterium*.

The terms "variant phosphoribosylpyrophosphate amidotransferase", "microorganism of the genus *Corynebacterium*", "culture", "homoserine or homoserine-derived L-amino acid" are as described above.

Still another aspect of the present disclosure provides use of the variant phosphoribosylpyrophosphate amidotransferase for the production of a purine nucleotide, or the preparation of a composition for producing a purine nucleotide.

Still another aspect of the present disclosure provides use of the polynucleotide for the production of a purine nucleotide, or the preparation of a composition for producing a purine nucleotide.

Still another aspect of the present disclosure provides use of the microorganism of the genus *Corynebacterium* for the production of a purine nucleotide, or the preparation of a composition for producing a purine nucleotide.

MODE FOR INVENTION

Hereinafter, the present disclosure will be described in more detail with reference to Examples. However, it is apparent to those skilled in the art to which the present disclosure pertains that these Examples are for illustrative purposes only, and the scope of the present disclosure is not intended to be limited by these Examples.

Example 1: Preparation of Wild-Type-Based IMP-Producing Strain

The wild-type strains of the genus *Corynebacterium* cannot produce IMP, or can produce IMP in very small amounts. Therefore, an IMP-producing strain was prepared based on wild-type *Corynebacterium stationis* ATCC6872. Specifically, the IMP-producing strain was prepared by weakening activity of purA, which encodes adenylosuccinate synthetase, and activity of guaB, which encodes 5'-inosinic acid dehydrogenase.

Example 1-1: Preparation of purA-Weakened Strain

In order to prepare a strain in which the start codon of purA was changed, an insertion vector containing purA was first prepared. In order to clone purA gene into the insertion vector, PCR was performed using the genomic DNA of *Corynebacterium stationis* ATCC6872 as a template and primers of SEQ ID NOS: 3 and 4 and SEQ ID NOS: 5 and 6 for 30 cycles of denaturation at 94° C. for 30 sec, annealing at 55° C. for 30 sec, and extension at 72° C. for 2 min. PCR was performed using two DNA fragments obtained by the above PCR as a template and primers of SEQ ID NOS: 3 and 6 for 30 cycles of denaturation at 94° C. for 30 sec, annealing at 55° C. for 30 sec, and extension at 72° C. for 2 min to obtain a DNA fragment. The obtained DNA fragment was digested with restriction enzyme XbaI, and cloned into a vector pDZ (Korean Patent No. 10-0924065 and International Patent Publication No. 2008-033001) that had been digested with the same enzyme. The vector prepared by the above method was designated as pDZ-purA-alt.

TABLE 1

| SEQ ID NO. | Primer name | (Sequence (5'-3')) |
|---|---|---|
| 3 | pDZ-purA(alt)-1 | GCTCTAGAGGCCACGATGCCCGGAGCATC |
| 4 | pDZ-purA(alt)-2 | TAACGATAGCTGCCAAGGTTATTCACTTCCTA-GATTT |
| 5 | pDZ-purA(alt)-3 | AGGAAGTGAATAACCTTGGCAGCTATCGT-TATCGTCG |

TABLE 1-continued

| SEQ ID NO. | Primer name | (Sequence (5'-3')) |
|---|---|---|
| 6 | pDZ-purA(alt)-4 | GCTCTAGAGGTCACGAATGGGTAGGTGCC |

The recombinant vector pDZ-purA-alt was transformed into *Corynebacterium stationis* ATCC6872 strain by electroporation, and then strains in which the vector was inserted into the chromosome by homologous recombination were selected on a medium containing 25 mg/L kanamycin. The primary strains thus selected were subjected to secondary crossover, and then selected strains were subjected to sequencing, thereby selecting a final strain into which the mutation was introduced. This strain was designated as ATCC6872-purA(alt).

Example 1-2: Preparation of guaB-Weakened Strain

In order to prepare a strain in which the start codon of guaB was changed, an insertion vector containing guaB was first prepared. In order to clone guaB gene into the insertion vector, PCR was performed using the genomic DNA of *Corynebacterium stationis* ATCC6872 as a template and primers of SEQ ID NOS: 7 and 8 and SEQ ID NOS: 9 and 10. PCR was also performed using the above PCR products as a template and primers of SEQ ID NOS: 7 and 10. The obtained DNA fragment was cloned in the same manner as in Example 1-1. The prepared vector was designated as pDZ-guaB-alt.

TABLE 2

| SEQ ID NO. | Primer name | (Sequence (5'-3')) |
|---|---|---|
| 7 | pDZ-guaB(alt)-1 | GCTCTAGACTACGACAACACGGTGCCTAA |
| 8 | pDZ-guaB(alt)-2 | CACGATTTTCGGT-CAATACGGGTCTTCTCCTTCGCAC |
| 9 | pDZ-guaB(alt)-3 | AGGAGAAGACCCGTATTGACCGAAAATCGTGTTTCT |
| 10 | pDZ-guaB(alt)-4 | GCTCTAGAATCGACAAGCAAGCCTGCACG |

The recombinant vector pDZ-guaB-alt was transformed into the ATCC6872-purA(alt) strain prepared in Example 1-1 by electroporation, and then strains in which the vector was inserted into the chromosome by homologous recombination were selected on a medium containing 25 mg/L kanamycin. The primary strains thus selected were subjected to secondary crossover, and then selected strains were subjected to sequencing, thereby selecting a final strain into which the mutation was introduced.

The finally selected IMP-producing strain based on wild-type *Corynebacterium stationis* ATCC6872 was designated as CJI9088.

Example 1-3: Fermentation Titer Test of CJI9088

2 mL of a seed culture medium was dispensed into test tubes with a diameter of 18 mm and autoclaved under pressure. Each of ATCC6872 and CJI9088 was inoculated and incubated at 30° C. for 24 h with shaking to be used as seed cultures. 29 mL of a fermentation medium was dispensed into 250 mL shaking Erlenmeyer flasks and autoclaved under pressure at 121° C. for 15 min, and 2 mL of the seed culture was inoculated and incubated for 3 days. Culture conditions were adjusted to a rotation speed of 170 rpm, a temperature of 30° C., and pH 7.5.

After completion of the culturing, IMP production was measured by HPLC (SHIMAZDU LC20A), and the culturing results are as in the following Table 3. The following results suggest that the purA- and guaB-weakened strains have IMP productivity.

TABLE 3

| Strain | IMP (g/L) |
|---|---|
| ATCC6872 | 0 |
| CJI9088 | 0.52 |

Seed culture medium: 1% glucose, 1% peptone, 1% meat extract, 1% yeast extract, 0.25% sodium chloride, 100 mg/L adenine, 100 mg/L guanine, pH 7.5

Fermentation medium: 0.1% sodium glutamate, 1% ammonium chloride, 1.2% magnesium sulfate, 0.01% calcium chloride, 20 mg/L iron sulfate, 20 mg/L manganese sulfate, 20 mg/L zinc sulfate, 5 mg/L copper sulfate, 23 mg/L L-cysteine, 24 mg/L alanine, 8 mg/L nicotinic acid, 45 µg/L biotin, 5 mg/L thiamine hydrochloric acid, 30 mg/L adenine, 1.9% phosphoric acid (85%), 2.55% glucose, 1.45% fructose Example 2: Identification of Phosphoribosylpyrophosphate Amidotransferase-Enhanced Variant In order to enhance activity of phosphoribosylpyrophosphate amidotransferase, which is the first enzyme in the IMP biosynthetic pathway, for the improvement of IMP productivity, a mutant library of purF, which is a gene encoding phosphoribosylpyrophosphate amidotransferase, was prepared, and an IMP productivity-enhancing mutation was identified.

Example 2-1: Preparation of purF-Containing Vector

In order to prepare a purF mutant library, a purF-containing recombinant vector was first prepared. PCR was performed using the genomic DNA of *Corynebacterium stationis* ATCC6872 as a template and primers of SEQ ID NO: 11 and SEQ ID NO: 12, and a PCR product was cloned into *E. coli* vector pCR2.1 by using a TOPO Cloning Kit (Invitrogen) to obtain pCR-purF.

TABLE 4

| SEQ ID NO. | Primer name | (Sequence (5'-3')) |
|---|---|---|
| 11 | purF tempF | AAGTTGATGCTTCAGGCACA |
| 12 | purF tempR | TGCAAGGATTGGCTCTTTGT |

Example 2-2: Preparation of purF Mutant Library

A purF mutant library was prepared based on the vector prepared in Example 2-1. The library was prepared by using an error-prone PCR kit (clontech Diversify® PCR Random Mutagenesis Kit). Under conditions where mutations may occur, PCR was performed using primers of SEQ ID NO: 13 and SEQ ID NO: 14. Specifically, under conditions where 0 to 3 mutations per 1000 bp may occur, pre-heating was performed at 94° C. for 30 sec, followed by 25 cycles of 94° C. for 30 sec and 68° C. for 1 min 30 sec. A PCR product thus obtained was subjected to PCR using a megaprimer (500 ng to 125 ng) for 25 cycles of 95° C. for 50 sec, 60° C. for 50 sec, and 68° C. for 12 min, and then treated with DpnI, and transformed into E. coli DH5a and spread on an LB solid medium containing kanamycin (25 mg/L). 20 kinds of transformed colonies were selected and then plasmids were obtained, followed by sequencing analysis. As a result, it was confirmed that mutations were introduced at different sites at a frequency of 2 mutations/kb. About 20,000 transformed E. coli colonies were taken and plasmids were extracted therefrom, and designated as a pTOPO-purF-library.

TABLE 5

| SEQ ID NO. | Primer name | (Sequence (5'-3')) |
|---|---|---|
| 13 | purF lib F | ACACGAGATAGCCCAGTGG |
| 14 | purF lib R | TCGTAGTTGCCATCAAAGCA |

Example 2-3: Evaluation of Prepared Library and Selection of Strain

The pTOPO-purF-library prepared in Example 2-2 was transformed into the CJI9088 strain prepared in Example 1 by electroporation, and then spread on a nutrient medium containing 25 mg/L kanamycin to obtain 10,000 colonies into which the mutant gene was inserted. The colonies were designated as CJI9088_pTOPO_purF(mt)1 to CJI9088_pTOPO_purF(mt)10000.
Nutrient medium: 1% peptone, 1% meat extract, 0.25% sodium chloride, 1% yeast extract, 2% agar, pH 7.2

Each of the obtained 10,000 colonies was inoculated in 200 μL of a seed culture medium autoclaved under pressure, and cultured in a 96-deep-well plate with shaking at 30° C. and 1200 rpm for 24 h by using a microplate shaker (TAITEC), and then used as a seed culture. 290 μL of fermentation medium autoclaved under pressure was dispensed into a 96-deep-well plate, and 20 μL each of the seed cultures was inoculated thereto, followed by culturing with shaking under the same conditions as above for 72 h.

In order to analyze production of 5'-inosinic acid in the culture medium, after completion of the culturing, 3 μL of culture supernatant was transferred to a 96-well UV-plate, each well containing 197 μL of distilled water. Next, a microplate reader was used to perform shaking for 30 sec, and a spectrophotometer was used to measure optical density at 25° C. and 270 nm and compared with the optical density of the CJI9088 strain to select 50 mutant strain colonies showing an increase of 10% or more in the optical density. Other colonies showed similar or decreased optical density compared to the control.

Optical densities of the 50 selected strains were measured in the same manner as above to repeatedly examine production amounts of 5'-inosinic acid. Two strains of CJI9088_pTOPO_purF(mt)201 and CJI9088_pTOPO_purF(mt)5674, which showed remarkable improvement in 5'-inosinic acid productivity compared to the CJI9088 strain, were selected.

Example 2-4: Identification of Mutation by Sequencing

In order to identify gene mutations of the mutant strains, each of CJI9088_pTOPO_purF(mt)201 and CJI9088_pTOPO_guaB(mt)5674 strains was subjected to PCR using primers of SEQ ID NOS: 15 and 16, followed by sequencing. Their purF genes were compared with those of the ATCC6872 and CJI9088 strains containing wild-type purF gene.

As a result, both of the strains were found to include purF gene mutation at different sites.

Specifically, it was confirmed that the CJI9088_pTOPO_purF(mt)201 strain has a substitution mutation of methionine for valine at position 2 in the purF amino acid sequence represented by SEQ ID NO: 2, and the CJI9088_pTOPO_purF(mt)5674 strain has a substitution mutation of arginine for glycine at position 445 in the purF amino acid sequence represented by SEQ ID NO: 2.

TABLE 6

| SEQ ID NO. | Primer name | (Sequence (5'-3')) |
|---|---|---|
| 15 | purF-seq-F | ACACGAGATAGCCCAGTGG |
| 16 | purF-seq-R | ACCAAGTCATCGACGCACATT |

In the following Examples 3 and 4, it was examined whether the above mutations affected IMP production of the microorganism of the genus Corynebacterium.

Example 3: Examination of IMP Productivity in CJI9088

The mutations identified in Example 2 were introduced into CJI9088, which is an ATCC6872-derived IMP-producing strain, and IMP productivity was examined.

Example 3-1: Preparation of Insertion Vector Containing purF Mutation

In order to introduce strains with the mutation selected in Example 2, an insertion vector was prepared. A vector for introduction of purF mutation is prepared as follows.

PCR was performed using the genomic DNA of ATCC6872 as a template and primers of SEQ ID NOS: 17 and 18 and SEQ ID NOS: 19 and 20. PCR was performed by denaturation at 94° C. for 5 min, and then, for 20 cycles of at 94° C. for 30 sec, at 55° C. for 30 sec, at 72° C. for 1 min, followed by polymerization at 72° C. for 5 min. PCR was performed using each of the resulting DNA fragments as a template and primers of SEQ ID NO: 17 and SEQ ID NO: 20. The resulting DNA fragment was digested with XbaI. By using T4 ligase, the DNA fragment was cloned into a linear pDZ vector which had been digested with restriction enzyme XbaI, and thus pDZ-purF(V2M) was prepared. PCR was performed using primers of SEQ ID NOS: 21 and 22, and SEQ ID NOS: 23 and 24 in the same manner as above. PCR was performed using each of the resulting DNA fragments as a template and primers of SEQ ID NO: 21 and SEQ ID NO: 24. The resulting DNA fragment was digested with XbaI. By using T4 ligase, the DNA fragment was cloned into a linear pDZ vector which had been digested with restriction enzyme XbaI, and thus pDZ-purF(G445R) was prepared.

TABLE 7

| SEQ ID NO. | Primer name | (Sequence (5-3)) |
|---|---|---|
| 17 | purF V2M 1F | GGGTCTAGAAGTACTGACCCGACCACTGCA |
| 18 | purF V2M 1R | TGGGGAAAGTAGTGTTCATCACGACGC |
| 19 | purF V2M 2F | TAGTAGAATCAGCGTCGTGATGAACAC |
| 20 | purF V2M 2R | GGGTCTAGATGGATTCCTGCCTCATTGACA |
| 21 | purF G445R 1F | GGGTCTAGACCGATGGCAAGACCTTGTACG |
| 22 | purF G445R 1R | CAAACCCTAAAGAGTCTGCTCTGATAGCTTC |
| 23 | purF G445R 2F | CAGTGTGCGAAGCTATCAGAGCAGACTCTT |
| 24 | purF G445R 2R | GGGTCTAGACAAGGTCATCGATGTAGCCATCG |

Example 3-2: Introduction of Mutant into CJI9088 Strain and Evaluation

CJI9088 was transformed with each of the pDZ-purF (V2M) and pDZ-purF(G445R) vectors prepared in Example 3-1, and strains in which the vector was inserted into the chromosome by homologous recombination were selected on a medium containing 25 mg/L kanamycin. The primary strains thus selected were subjected to secondary crossover to select strains into which the target gene mutation was introduced. Introduction of the gene mutation into the final transformed strains was examined by PCR using primers of SEQ ID NO: 15 and SEQ ID NO: 16, and then sequencing was performed to confirm introduction of the mutation into the strains. Specifically, the strain introduced with V2M mutation of purF gene was designated as CJI9088_purF_m1, and the strain introduced with G445R mutation of purF gene was designated as CJI9088_purF_m2. Further, in order to prepare a mutant strain having both of V2M and G445R mutations, CJI9088_purF_m1 strain was transformed with the pDZ-purF(G445R) vector, and colonies were obtained in the same manner as above. Through sequencing analysis of the obtained colonies, a strain introduced with both of V2M and G445R mutations of purF gene was selected and designated as CJI9088_purF_m1m2.

As shown in the results below, the CJI9088_purF_m1 or CJI9088_purF_m2 strain having V2M mutation or G445R mutation in the purF gene showed IMP concentration of 0.15 g/L (128%) or 0.09 g/L (117%), respectively, indicating improvement compared to the control CJI9088 strain. Further, the CJI9088_purF_m1m2 strain having both of V2M and G445R mutations showed IMP concentration improvement of 0.31 g/L (159%), indicating that when both of the two mutations are included, most effective improvement may be obtained in IMP concentration.

TABLE 8

| Strain | IMP (g/L) |
|---|---|
| CJI9088 | 0.52 |
| CJI9088_purF_m1 | 0.67 |
| CJI9088_purF_m2 | 0.61 |
| CJI9088_purF_m1m2 | 0.83 |

Example 4: Examination of IMP Productivity in ATCC6872-Derived IMP-Producing Strain To examine the effect of the purF mutant which was identified in Example 2, based on a strain producing a high concentration of IMP, the mutant was introduced into CJI0323 (Accession No. KCCM12151P, Korean Patent No. 10-1904675), which is a strain producing a high concentration of IMP, and IMP productivity was examined.

Example 4-1: Introduction of Mutant into CJI0323 Strain and Evaluation

CJI0323 was transformed with each of the pDZ-purF (V2M) and pDZ-purF(G445R) vectors prepared in Example 3-1, and strains in which the vector was inserted into the chromosome by homologous recombination were selected on a medium containing 25 mg/L kanamycin. The primary strains thus selected were subjected to secondary crossover to select strains into which the target gene mutation was introduced. Introduction of the gene mutation into the final transformed strains was examined by PCR using primers of SEQ ID NO: 15 and SEQ ID NO: 16, and then sequencing was performed to confirm introduction of the mutation into the strains. Specifically, the strain introduced with V2M mutation of purF gene was designated as CJI0323_purF_m1, and the strain introduced with G445R mutation of purF gene was designated as CJI0323_purF_m2. Further, in order to prepare a mutant strain having both of V2M and G445R mutations, CJI0323_purF_m1 strain was transformed with the pDZ-purF(G445R) vector, and colonies were obtained in the same manner as above. Through sequencing analysis of the obtained colonies, a strain introduced with both of V2M and G445R mutations of purF gene was selected and designated as CJI0323_purF_m1m2.

The CJI0323_purF_m1 was called CJI2353, deposited at the Korean Culture Center of Microorganisms on Sep. 10, 2018, under the provisions of the Budapest Treaty, and assigned accession number KCCM12316P. Further, the prepared CJI0323_purF_m2 was called CJI2354, deposited at the Korean Culture Center of Microorganisms on Sep. 10, 2018, under the provisions of the Budapest Treaty, and assigned accession number KCCM12317P.

As shown in the results below, the CJI0323_purF_m1 or CJI0323_purF_m2 strain having V2M mutation or G445R mutation in the purF gene showed IMP concentration of 1.9 g/L (119%) or 0.95 g/L (109%), respectively, indicating improvement compared to the control CJI0323 strain. Further, the CJI0323_purF_m1m2 strain having both of V2M and G445R mutations showed IMP concentration improvement of 3.33 g/L (134%), indicating that when both of the two mutations are included, most effective improvement may be obtained in IMP concentration.

TABLE 9

| Strain | IMP (g/L) |
| --- | --- |
| CJI0323 | 9.52 |
| CJI0323_purF_m1 | 11.42 |
| CJI0323_purF_m2 | 10.47 |
| CJI0323_purF_m1m2 | 12.85 |

Example 5: Examination of 5'-Xanthylic Acid Productivity of purF Mutant

To examine the effect of the purF mutant which was identified in Example 2, based on a XMP-producing strain, the mutant was introduced into KCCM10530 (Korean Patent Publication No. 10-2005-0056670), which is a strain producing a high concentration of XMP, and XMP productivity was examined.

Example 5-1: Introduction of Mutant into KCCM10530 Strain and Evaluation

KCCM10530 was transformed with each of the pDZ-purF (V2M) and pDZ-purF(G445R) vectors prepared in Example 3-1, and strains in which the vector was inserted into the chromosome by homologous recombination were selected on a medium containing 25 mg/L kanamycin. The primary strains thus selected were subjected to secondary crossover to select strains into which the target gene mutation was introduced. Introduction of the gene mutation into the final transformed strains was examined by PCR using primers of SEQ ID NO: 15 and SEQ ID NO: 16, and then sequencing was performed to confirm introduction of the mutation into the strains. Specifically, the strain introduced with V2M mutation of purF gene was designated as KCCM10530_purF_m1, and the strain introduced with G445R mutation of purF gene was designated as KCCM10530_purF_m2. Further, in order to prepare a mutant strain having both of V2M and G445R mutations, KCCM10530_purF_m1 strain was transformed with the pDZ-purF(G445R) vector, and colonies were obtained in the same manner as above. Through sequencing analysis of the obtained colonies, a strain introduced with both of the V2M and G445R mutations of purF gene was selected and designated as KCCM10530_purF_m1m2.

KCCM10530_purF_m1 was called CJX1681, deposited at the Korean Culture Center of Microorganisms on Sep. 10, 2018, under the provisions of the Budapest Treaty, and assigned accession number KCCM12312P. Further, the prepared KCCM10530_purF_m2 was called CJX1682, deposited at the Korean Culture Center of Microorganisms on Sep. 10, 2018, under the provisions of the Budapest Treaty, and assigned accession number KCCM12313P.

As shown in the results below, the KCCM10530_purF_m1 or KCCM10530_purF_m2 strain having V2M mutation or G445R mutation in the purF gene showed XMP concentration of 1.77 g/L (115%) or 0.8 g/L (107%), respectively, indicating improvement, as compared with the control KCCM10530 strain. Further, the KCCM10530_purF_m1m2 strain having both of V2M and G445R mutations showed XMP concentration improvement of 2.36 g/L (120%), indicating that when both of the two mutations are included, the most effective improvement may be obtained in XMP concentration.

TABLE 10

| Strain | IMP (g/L) |
| --- | --- |
| KCCM10530 | 11.8 |
| KCCM10530_purF_m1 | 13.57 |
| KCCM10530_purF_m2 | 12.68 |
| KCCM10530_purF_m1m2 | 14.16 |

Based on the above description, it will be understood by those skilled in the art that the present disclosure may be implemented in a different specific form without changing the technical spirit or essential characteristics thereof. Therefore, it should be understood that the above embodiments are not limitative, but illustrative in all aspects. The scope of the present disclosure is defined by the appended claims rather than by the description preceding them, and therefore all changes and modifications that fall within the metes and bounds of the claims, or equivalents of such metes and bounds are therefore intended to be embraced by the claims.

The invention claimed is:

1. A variant phosphoribosylpyrophosphate amidotransferase comprising SEQ ID NO: 2 and having a substitution selected from the group consisting of, i) methionine is substituted for the amino acid at position 2, ii) arginine is substituted for the amino acid at position 445, and iii) methionine is substituted for the amino acid at position 2 and arginine is substituted for the amino acid at position 445.

2. A polynucleotide encoding the variant phosphoribosylpyrophosphate amidotransferase of claim 1.

3. A vector comprising the polynucleotide of claim 2.

4. A microorganism of the genus *Corynebacterium* producing a purine nucleotide, the microorganism comprising the variant phosphoribosylpyrophosphate amidotransferase of claim 1.

5. The microorganism of the genus *Corynebacterium* producing a purine nucleotide of claim 4, wherein the microorganism of the genus *Corynebacterium* is *Corynebacterium stationis*.

6. A method of preparing a purine nucleotide, comprising the step of culturing the microorganism of the genus *Corynebacterium* of claim 4 in a medium.

7. The method of preparing a purine nucleotide of claim 6, further comprising the step of recovering the purine nucleotide from the microorganism or the medium after the step of culturing.

8. The method of preparing a purine nucleotide of claim 6, wherein the microorganism of the genus *Corynebacterium* is *Corynebacterium stationis*.

* * * * *